United States Patent [19]

Calam et al.

[11] Patent Number: 5,011,688

[45] Date of Patent: Apr. 30, 1991

[54] LIQUID COMPOSITION FOR THE RELIEF OF PREMENSTRUAL AND MENSTRUAL DISCOMFORTS

[76] Inventors: Henry D. Calam, 251 Furnace Dock Rd., Peekskill, N.Y. 10566; Hans A. Schaeffer, 14 Pallant Ave., Linden, N.J. 07036

[21] Appl. No.: 523,036

[22] Filed: May 8, 1990

Related U.S. Application Data

[63] Continuation-in-part of Ser. No. 309,078, Feb. 2, 1989, abandoned, which is a continuation of Ser. No. 74,548, Jul. 17, 1987, abandoned.

[51] Int. Cl.$^5$ .................... A61K 9/08; A61K 47/00
[52] U.S. Cl. .................... 424/195.1; 426/592; 514/783; 514/869; 514/872; 514/899; 514/922; 514/935
[58] Field of Search .............. 424/195.1, 10; 514/783, 514/974, 872, 899, 869, 922, 935; 426/592

[56] References Cited

U.S. PATENT DOCUMENTS

| | | | |
|---|---|---|---|
| 47,204 | 4/1865 | Hellman | 424/195.1 |
| 74,940 | 2/1868 | Rambaut | 424/195.1 |
| 83,273 | 10/1868 | Fullerton | 424/195.1 |
| 262,744 | 8/1882 | Cornwell | 424/195.1 |
| 282,898 | 8/1883 | Jacobs | 424/195.1 |
| 302,995 | 8/1884 | Fuller | 424/195.1 |
| 325,586 | 9/1885 | Bunting | 424/195.1 |
| 350,988 | 10/1886 | Owings | 424/175.1 |
| 411,921 | 10/1889 | Ingle | 424/195.1 |
| 416,473 | 12/1889 | Lorenz | 424/195.1 |
| 2,991,180 | 7/1961 | Faure | 426/592 |
| 3,050,397 | 8/1962 | Carroll | 426/592 |
| 3,558,325 | 1/1971 | Recsei | 426/592 |
| 3,843,809 | 10/1974 | Luck | 426/592 |
| 4,001,458 | 1/1977 | Murulo | 426/592 |
| 4,414,231 | 11/1983 | Ficca | 426/592 |
| 4,466,960 | 8/1984 | Silverman et al. | 514/226.2 |
| 4,888,343 | 12/1989 | Jones et al. | 514/264 |

OTHER PUBLICATIONS

Derwent Abstract of Belg. 902323 (Aug. 16, 1985) Marakakis.
Derwent Abstract of USSR 806758 (Feb. 25, 1981) AS UZB Botanical.
Derwent Abstract of USSR 863631 (Sept. 15, 1981) Mosc Liquor-Water.
Derwent Abstract of USSR 1244174 (Jul. 15, 1986) Fermentation Prods.
Derwent Abstract of USSR 962299 (Sept. 30, 1982) Brew Prod. Res. Ins. Kash.
Derwent Abstract of USSR 885246 (Nov. 30, 1981) Magarach Wine Makintikh.
Derwent Abstract of USSR 963495 (Oct. 7, 1982) Pacific Ocean Bioor. Vlad.

*Primary Examiner*—Shep K. Rose
*Attorney, Agent, or Firm*—Curtis, Morris & Safford

[57] ABSTRACT

A liquid composition for the relief of premenstrual and menstrual discomfort comprising, as active pharmaceutical agents, an effective amount of an analgesic, an antihistamine, and a diuretic, said active agents being dissolved in a liquid vehicle, said composition containing 5-25 percent by volume alcohol and being flavored with active flavoring elements selected from the group consisting of citrus, vanilla, and mint, said active flavoring ingredients being present in an amount sufficient to mask the unpleasant taste of the pharmaceutically active agents.

12 Claims, No Drawings

LIQUID COMPOSITION FOR THE RELIEF OF PREMENSTRUAL AND MENSTRUAL DISCOMFORTS

This application is a continuation-in-part of copending application, Ser. No. 07/309,078, filed Feb. 2, 1989, which application was a continuation of copending application Ser. No. 07/074,548, filed July 17, 1987, both now abandoned.

This invention relates broadly to a liquid composition for the relief of premenstrual and menstrual discomforts and dysmenorrhea. More specifically, it relates to a liquid medicine comprising a known combination of active pharmaceutical agents, e.g., an analgesic, an antihistamine, and a diuretic, in combination with a unique combination of flavoring ingredients which effectively mask the unpleasant taste of the active pharmaceutical agents.

BACKGROUND OF THE INVENTION

Premenstrual syndrome (PMS) is the term in common use to describe the complex of physical and mental symptoms which occur from seven to fourteen days prior to the onset of the menstrual flow. Menstrual discomforts include primary dysmenorrhea which includes painful menstruation and cramping.

Menstruation occurs in women from the age of twelve to thirteen years to, on the average, forty-seven years of age. It occurs at more or less regular intervals, except during pregnancy and lactation. The normal menstrual cycle averages twenty-eight days with some variation based on the woman's age, physical and emotional well being, and other factors. The duration of menstrual flow is variable but usually between three and seven days.

The symptoms of premenstrual syndrome are varied and may range from mild to incapacitating. As many as seventy to ninety percent of all menstruating women have recurrent premenstrual symptoms and as many as twenty to forty percent suffer some degree of temporary mental or physical incapacitation. The psychological symptoms include irritability, lethargy, depression, anxiety, sleep disorders, crying spells, and hostility. The neurological symptoms include headaches, dizziness, fainting, and seizures. Among the physical symptoms are tenderness and swelling in the breasts, constipation, abdominal bloating and cramping, edema in the extremities, less frequent urination, and acne.

The physical, neurological, and psychological symptoms of premenstrual syndrome and dysmenorrhea are a major cause of discomfort to women, and cause substantial loss of time and efficiency in the workplace. The art has attempted to address these problems in a number of nonprescription pharmacological compositions for the treatment of premenstrual and menstrual discomforts without completely successful results.

Most nonprescription products contain either aspirin or acetaminophen as the analgesic. Aspirin and acetaminophen are believed to have equivalent analgesic efficacy for the diminution of headache and other minor pains. Their relative efficacy for relieving premenstrual and menstrual pain has not been determined. Nevertheless, both agents are routinely used for diminishing menstrual pain. Another analgesic frequently recommended is ibuprofen.

Most nonprescription products also contain an antihistamine such as pyrilamine maleate. They also contain diuretics in an amount which would be subtherapeutic if taken separately. The most frequently used diuretics are ammonium chloride, caffeine, and pamabrom.

Among the compositions available to provide relief from one or more of the symptoms of premenstrual syndrome and menstrual discomforts are the commercial products Midol, Midol PMS, Pamprin, and Premensyn PMS. Midol is essentially an aspirin tablet containing caffeine and an antispasmodic ingredient. Midol PMS, Premensyn PMS, and Pamprin all contain acetaminophen, a diuretic, and an antihistamine. All of these active ingredients are considered safe and effective in combination.

Although the commercially available compositions are useful to relieve symptoms of premenstrual syndrome and menstrual discomforts, none are completely effective. Liquid compositions would be desirable because a liquid vehicle speeds the action of both the analgesic and the diuretic and potentiates the active ingredients. Moreover, many persons have difficulty swallowing medications in solid form.

The problem facing the art, however, is that liquids containing analgesic, antihistamine, and diuretic active pharmaceutical agents taste terrible and pharmaceutical chemists have heretofore failed to satisfactorily mask the bitter principals and aftertaste. No patentable liquid products containing this combination of actives are available in the market.

The solid compositions now on the market for relief of premenstrual and menstrual discomfort, including uncoated and chewable tablets, typically taste bitter and metallic. It has always been a difficult challenge for the pharmaceutical chemist in compounding over-the-counter medicines to mask the bitter, metallic, and otherwise unpleasant tastes and lingering aftertastes of many active pharmaceutical agents. This is a particular problem when a liquid dosage form is desirable because in liquid dosage forms the bad taste is usually more apparent than in solid dosage forms including uncoated tablets. It is recognized among pharmaceutical chemists and physicians that patients' compliance with a dosage schedule is of paramount importance for controlling the symptoms and accordingly the organoleptic properties of any medicine must be such that the patient's resistance to following a schedule of administration is minimized.

Among the worst tasting active pharmaceutical agents in over-the-counter medicines, and particularly medicinal liquids, are analgesics, antihistamines, antitussives, sedatives, and others. When these agents are used in combination with one another, the problem is exacerbated. A number of products have failed in the marketplace when patients have refused to take repeat doses even though the active pharmaceutical ingredients were effective for the intended purpose.

Among the ingredients used by pharmaceutical chemists to mask the bitterness of the active pharmaceutical agents are licorice, anise, anethol, glycerrhizins such as ammonium glycerrhizin, etc., vanillin, ethyl vanillin, methyl salicylate, and menthol and other mild surface anesthetics. The purpose of these flavoring ingredients is to interact with the bitter principals of the active pharmaceutical agents and to deceive the taste receptors in the mouth. These ingredients have typically fallen short of masking the taste of active pharmaceutical agents, particularly those with strong bitter aftertastes. These aftertastes remain in the mouth long after the initial impact of the medicine which may have been successfully masked.

OBJECTS OF THE INVENTION

It is a primary object of the invention to provide a liquid pharmaceutical composition designed for the relief of a broad spectrum of symptoms associated with premenstrual syndrome.

It is still a further object of this invention to provide a pharmaceutical unit dose in liquid form desirably for nighttime administration, but for daytime use as well, which delivers an effective amount of an analgesic, an antihistamine, and a diuretic to a patient.

It is still a further object of this invention to provide a pharmaceutical dose in liquid form, of an effective composition for relief of symptoms of premenstrual and menstrual discomforts which tastes pleasant and which contains flavor ingredients which mask the bitter principals of the active pharmaceutical agents and deceive the taste receptors in the mouth.

THE INVENTION

These an other objects of the invention are achieved in a liquid composition for the relief of premenstrual syndrome which comprises, as active pharmaceutical agents, an analgesic, an antihistamine, and a diuretic. These active ingredients are dissolved in a liquid vehicle which contains alcohol in from 5 to 25 percent by volume and preferably from 12 to 25 percent by volume of the total composition. The liquid composition is flavored with active flavoring elements selected from the group consisting of citrus, vanilla, and mint, the active elements being present in an amount sufficient to mask the unpleasant taste of the pharmaceutically active agents.

In the preferred embodiments of the invention, the active pharmaceutical agents are acetaminophen as the analgesic, pyrilamine maleate as the antihistamine, and pamabrom as the diuretic. The liquid compositions of the invention contain a citrus flavoring ingredient in from 0.02 to 0.31 percent by weight of the composition. The vanilla flavoring is present in from 0.05 to 1.5 percent by weight of the composition. The mint flavoring ingredient is present in an amount sufficient to mask the taste of the pharmaceutically active agents but in an amount of from 0.02 to 0.16 percent by weight, the lower amount being sufficient to neutralize the flavor receptors in most regions of the mouth and consequently allow the passage of the unpleasant principals without detection, and the higher amount being still less than that amount which would be detected by the subject. Desirably the liquid compositions also contain at least 30 percent corn syrup or other sweetening syrups.

Suitable compositions and dosages of the active agents are well known in the art and have been approved by the Food and Drug Administration. They are described in the Federal Register, "DEPARTMENT OF HEALTH AND HUMAN SERVICES, Food and Drug Administration, 21 CFR Part 357 (Docket No. 82N-0165), *Orally Administered Menstrual Drug Products for Over-the-Counter Human Use; Establishment of a Monograph,* Agency: Food and Drug Administration; Action: Advance notice of proposed rulemaking."—the "Monograph," Volume 47, No. 235, Tuesday, Dec. 2, 1982, at 55076–55101.

With respect to dosage, a preferred composition will comprise a one ounce dose to be taken four times per day, thereby providing the maximum daily dosage per the Monograph. Other compositions may provide the same maximum daily dosage in one-half to two ounce doses, again in accordance with "Monograph."

With respect to the flavorings, the citrus flavors are included for their bridging characteristics, pleasant top notes, high volatility, and good initial coverage. The vanilla flavoring ingredients, e.g., butterscotch, are included for their good volatility, their ability to be blended with bitter notes, their intermediate duration, and their excellent smoothing of incompatible metallic notes. The mints are included for their mild and temporary anesthetic action, i.e., they mask the bitter notes of the active pharmaceutical agents, particularly the antihistamines, but they are not perceived by most subjects. It is critical to the invention that the several groups be employed in proper balance.

The combination of flavoring components is critical to the composition and to its utility as a pharmaceutical product intended for regular consumption. The critical combination of flavoring components was determined after substantial empirical, trial and error research. While reference to the pharmaceutical literature was made, significant departures from the standard recommendations of that literature were made in making the invention.

It was understood that the intended product containing the three active ingredients described above would be compounded in a pharmaceutical vehicle containing corn syrup and alcohol. It was realized that the task of masking the offensive flavors of the three medicaments would be extremely difficult but it was also recognized that unless those flavors could be masked, women would not repeatedly consume the compositions every four weeks or so and the product would have no practical value.

As a first step, it was noted that acetaminophen displays bitter, acrid and sour notes which cannot be covered by sweetening agents; that pyrilamine maleate is bitter but that it also has a strong, lingering metallic aftertaste, not unlike the taste of copper salts; and that Pamabrom is sour, quite salty and bitter. Moreover, it was recognized that even at very low concentrations, substantially lower than the intended dosage, the combination of actives displays an even more intense and longer lasting acrid bitterness than do the individual components. This amplified intensity and longer lasting acrid bitterness may be explained by the fact that bitter and acidic taste receptors are located on the upper surface at the tip of the tongue, thereby enhancing the sensitivity to the impact of these taste notes.

Reference was then made to the pharmaceutical literature. The references consulted included: L. Lachman, H. Lieberman and J. Kanig, *The theory of Praxis of Industrial Pharmacy,* 2d Edition, 1976, Lea & Febiger, Philadelphia, Pa.; *Remington's Pharmaceutical Sciences,* 15th Edition, 1975, Mack Publishing Co, Easton, Pa.; *Flavor Research and Food Acceptance,* Arthur D. Little, 1958, Reinhold Publishing Co., N.Y.; and published and unpublished flavoring guides distributed by several fragrance and flavor suppliers.

Lachman et al, pages 541–566, recommends a series of masking flavors, including wild cherry, walnut, chocolate, passion fruit, mint, spice and anise. These and other similar flavors were obtained from flavor suppliers and incorporated in the test compositions. Several of these were given to a taste panel consisting of twelve women of ages 16 to 45. All of the compositions tested were unanimously and emphatically rejected by the panelists. Thus it was found that for this particularly intensely distasteful mixture of active components, departures had to be made from the recommendations of Lachman et al.

Reference was then made to Remington, page 1227 et. seq., which suggests an even larger number of flavoring agents in addition to those mentioned in Lachman et al. These encompass nearly all of the commonly used flavoring agents. Experiments were carried out with flavored compositions containing cocoa syrup, raspberry, cinnamon, orange syrup, licorice syrup and aromatic elixir. Again, the panel rejected all of the flavored compositions as being unacceptably distasteful. Nevertheless, some satisfaction was expressed by some panelists with respect to compositions containing the citrus, which apparently covered some of the taste of the acidic and sour/salty tasting active ingredients.

Based on this preliminary lead, the inventors pursued the citrus flavor (orange) by combining it with lemon oils to further enhance the top notes and improve the overall volatility of the flavor blend. Since the tests indicated that citrus flavors alone would not mask all of the intense and disagreeable flavors of the three-component mixture of active ingredients, further tests were carried out with further flavoring components which would serve as masking agents of bitter principals. The masking agents which were included in further experimental compositions included: ammoniated glycerrhizin (a licorice derivative), Veltol, a proprietary vanillin compound (Pfizer) and Magnasweet, another proprietary vanillin-based composition (Food Materials). The panelists reacted somewhat more positively to the compositions containing both enhanced citrus flavors and the vanillin-based masking flavors.

The essentially two-component flavoring mixture was then subjected to further experimentation. In particular, ethylvanillin was compounded with caramel-type flavors to produce a pronounced butterscotch effect and this blend was added to the orange-lemon flavors using different ratios. The panelists confirmed a definite improvement and noted that the bitterness of the composition was substantially masked. However, the lingering metallic aftertaste due to the pyrilamine maleate, was still recognized by a majority of the panel members and it was clear that further efforts would be necessary to obtain a flavoring composition which would satisfactorily mask the worst flavors of the active ingredients.

In a next series of experiments, it was determined that the way to overcome the bitterness of the pyrilamine maleate was to include in the composition a mild surface anesthetic for the flavor receptors. Menthol, a common flavoring additive for that purpose, was attempted but even at extremely low concentrations it proved to be incompatible with the other constituents. The flavor combinations produced an unacceptable and odd flavor mix.

Mint oils were then tested for their efficacy as mild surface anesthetics for the flavor receptors. After considerable testing it was found that mint flavorings, when employed at concentrations below that at which they were detectable as an individual flavor component, i.e., at subliminal concentrations, nevertheless served as an excellent mask of the metallic aftertaste of the composition.

Compositions containing the active ingredient, corn syrup, alcohol, and the three flavors described, were again given to the panel for evaluation. The result was unanimous approval by the panelists. In order to investigate how the consumer would react to repetitive use of the product, the panelists were given repeated doses for three to five days of normal use, each panelist receiving a sufficient supply of the composition with an instruction to consume one full dose (one ounce) daily before bedtime for a period of five days. The panelists reported that the product was satisfactory.

An additional test was repeated with 51 additional subjects. In total, 63 subjects consumed the test compositions. The results of these tests are summarized in the following table:

|  | Good to Excellent | Fair | Poor |
|---|---|---|---|
| overall taste impression | 88.9% | 7.9% | 3.2% |
| mouthfeel | 96.8 | 1.6 | 1.6 |
| sweetness | 100.0 | — | — |
| absence of unpleasant aftertaste | 85.7 | 7.9 | 6.4 |

PREFERRED COMPOSITIONS

The preferred compositions and concentrations of the several flavor ingredients are set forth below. All percentages are by weight of the individual flavoring ingredient.

| Component | | | (% by Wt.) Range | (% by Wt.) Preferred |
|---|---|---|---|---|
| (A) | citrus: | | | |
| | (1) | orange: oil of Valencia | | |
| | | orange, terpeneless | 20–50 | 30–40 |
| | | citral | 5–20 | 8–12 |
| | | geraniol | 2–5 | 2.5–4.0 |
| | | d-limonene | 1–10 | 2.5–6.5 |
| | | geraniol acetate | 1–3 | 1.5–2.0 |
| | | rhodinal | 0.5–2 | 0.7–1.2 |
| | | linalool | 0.2–2 | 0.5–1.2 |
| | | linalyl acetate | 1.5–6 | 2.5–4 |
| | | ethyl alcohol | q.s. (quantity sufficient) | |
| | (2) | lemon: | | |
| | | oil of lime, terpeneless | 3–15 | 5–8 |
| | | citral | 2–10 | 3–6 |
| | | geraniol | 0.1–0.5 | 0.2–0.4 |
| | | aldehyde C8 | 0.1–1 | 0.3–0.7 |
| | | aldehyde C12 | 0.1–1 | 0.3–0.7 |
| | | nerol | 0.1–1 | 0.2–1.2 |
| | | rhodinal | 0.1–2.0 | 0.2–1.2 |
| | | oil of lemon, terpeneless | 1–10 | 2–6 |
| | | geraniol acetate | 1–3 | 1.5–2.5 |
| | | d-limonene | 0.1–2 | 0.2–1.2 |
| | | linalool | 0.1–2.5 | 0.3–1.8 |
| | | benzyl butyrate | 2–10 | 3–6 |
| | | ethyl alcohol | q.s. | |
| (B) | vanilla-butterscotch | | | |
| | | ethyl maltol | 1–6 | 2–5 |
| | | vanillin | 1–10 | 2–6 |
| | | ethyl vanillin | 0.1–5 | 0.2–1.5 |
| | | heliotropin | 0.1–5 | 0.2–1.5 |
| | | cyclotene | 0.1–4 | 0.3–1.5 |
| | | propyleneglycol | q.s. | |
| | | ethyl butyrate | 1–8 | 2–5 |
| | | diacetyl ketone | 1–8 | 2–5 |
| (C) | mint: | | | |
| | | peppermint oil Chinese, specially fractionated | 0.5–10 | 1.5–3.5 |

-continued

| Component | (% by Wt.) Range | (% by Wt.) Preferred |
|---|---|---|
| spearmint oil | 0.1–5 | 0.5–2.0 |
| l-menthol | 10–60 | 35–50 |
| l-menthone | 0.1–2 | 0.2–1.5 |
| l-carvone | 0.1–3 | 0.4–2 |
| cineole | 0.1–2 | 0.2–1 |
| isomenthone | 0.1–1 | 0.2–0.5 |
| l-limonene | 0.1–2 | 0.2–1.5 |
| ethyl alcohol | q.s. | |

The citrus ingredients are desirably present in from 0.02 to 0.31 percent of the total liquid composition. The vanilla flavoring ingredient is desirably present in from 0.05 to 1.5 percent of the total composition, and the mint flavoring is present in a subliminal amount, i.e., an amount greater than that necessary to mask the unpleasant taste of the active pharmaceutical agents but less than the taste threshold for mint of the ultimate subject. The mint ingredient is preferably contained in an amount from 0.02 to 0.16 percent by weight of the total liquid composition.

The citrus ingredient preferably comprises 0.05 to 0.20 percent of orange ingredient and from 0.05 to 0.16 percent by weight of lemon ingredient. Still better results are obtained where the orange ingredient is present in from 0.07 to 0.12 percent by weight and the lemon ingredient is present in from 0.03 to 0.14 percent by weight of the liquid composition.

The following examples are representative of the compositions of the invention and the methods which may be employed to prepare liquid compositions according to the invention.

EXAMPLE I

A liquid mixture is prepared having the following composition.

| Component | Label Claim | Overage | Gms/Liter |
|---|---|---|---|
| (1) ethyl alcohol 95%, USP | 25% v/v (100% ethanol) | 2% | 218.7 |
| propyleneglycol, USP | | | 72.5 |
| acetaminophen, USP | 1000 mgs/fl. oz | 2% | 34.6 |
| methylparaben | | | 1.0 |
| propylparaben | | | 0.15 |
| (2) demin. water | | | 102.4 |
| pyrilamine maleate, USP | 30 mgs/fl. oz | 2% | 1.04 |
| citric acid, anh, USP | | | 1.50 |
| (3) demin. water | | | 102.4 |
| pamabrom | 50 mgs/fl. oz | 2% | 1.73 |
| (4) high fructose corn syrup (sp. gr. 1.321) | | | 599.73 |
| (5) flavors: | | | |
| natural and artificial orange | | | 0.99 |
| natural and artificial lemon | | | 1.15 |
| natural and artificial mint | | | 0.69 |
| natural and artificial butterscotch | | | 3.39 |
| sodium saccharin | | | 1.80 |
| (6) color solutions | | | 1.76 |
| | | | 1,145.53 |

The foregoing composition is made according to the following method. The alcohol and propylene glycol are added to a first stainless steel mixing vessel equipped with a stainless steel agitator and explosion-proof motor. The alcohol and propyleneglycol are agitated and the acetaminophen, methylparaben, and propylparaben are added. Agitation is continued until a clear solution is obtained. Demineralized water and pyrilamine maleate are added to a second stainless steel mixing vessel and agitated until the pyrilamine maleate is dissolved. The aqueous solution of pyrilamine is then added to the solution of acetaminophen and parabens in the solution in the first mixing vessel. Demineralized water and pamabrom are then mixed in the second vessel until the pamabrom is dissolved and that solution is also added to the mixture in the first vessel. Corn syrup is added to the first vessel and the mixture is agitated taking care that no crystallized fructose remains in the storage containers. Thereafter, the flavors, sodium saccharin, and color solutions are added to match the flavor and color of the desired end product. The mixture is agitated until homogeneous. The final product is clear and has a vanilla (butterscotch) citrus flavor and odor. It is free of particles of suspended matter.

It has been determined that the objectionable bitter aftertastes found in liquid preparations including these active pharmaceutical agents have virtually been eliminated in the unique compositions employing the combination of flavor masking agents of this invention. Taste testing results have been highly positive in terms of overall taste, mouth feel, and sweetness, as well as the absence of unpleasant aftertastes.

Women have reported that this composition has provided satisfactory results in relieving a wide range of premenstrual and menstrual discomforts. Women report the liquid is easy to swallow and relief from discomforts is fast and complete. Daytime use of the composition affords the user highly satisfactory results in relief of PMS and menstrual discomforts. The benefits of the composition are seen as particularly important at bedtime, when unrelieved premenstrual and menstrual discomfort may make a good night's sleep impossible.

EXAMPLE II

A liquid mixture is prepared essentially according to the method of Example I, having the following composition.

| Component | Label Claim | Overage | Gms/Liter |
|---|---|---|---|
| (1) ethyl alcohol 95%, USP | 12.5% v/v (100% ethanol) | 2% | 115.0 |
| propyleneglycol, USP | | | 72.5 |
| acetaminophen, USP | 500 mgs/fl. oz | 2% | 17.3 |
| benzoic acid | | | 2.0 |
| (2) demin. water | | | 102.4 |
| pyrilamine maleate, USP | 25 mgs/fl. oz | 2% | 0.90 |
| citric acid, anh, USP | | | 1.00 |
| (3) demin. water | | | 102.4 |
| pamabrom | 50 mgs/fl. oz | 2% | 1.73 |
| (4) high fructose corn syrup (sp. gr. 1.321) | | | 726.65 |
| (5) flavors: | | | |
| natural and artificial orange | | | 0.90 |
| natural and artificial lemon | | | 1.00 |
| natural and artificial mint | | | 0.70 |
| natural and artificial cherry | | | 2.80 |
| sodium saccharin | | | 1.50 |
| (6) color solutions | q.s. | | 1.75 |
| | | | 1,150.53 |

EXAMPLE III

A liquid mixture is prepared essentially according to the method of Example I, having the following composition.

| Component | Label Claim | Over-age | Gms/Liter |
|---|---|---|---|
| (1) ethyl alcohol 95%, USP | 6.25% v/v (100% ethanol) | 2% | 57.5 |
| propyleneglycol, USP | | | 70.0 |
| acetaminophen, USP | 750 mgs/fl. oz | 2% | 26.0 |
| benzoic acid | | | 2.0 |
| (2) demin. water | | | 102.4 |
| pyrilamine maleate, USP | 30 mgs/fl. oz | 2% | 1.04 |
| citric acid, anh, USP | | | 1.50 |
| (3) demin. water | | | 102.4 |
| pamabrom | 50 mgs/fl. oz | 2% | 1.73 |
| (4) high fructose corn syrup (sp. gr. 1.321) | | | 693.68 |
| (5) flavors: | | | |
| natural and artificial orange | | | 1.05 |
| natural and artificial lemon | | | 0.80 |
| natural and artificial mint | | | 0.70 |
| natural and artificial chocolate | | | 2.55 |
| sodium saccharin | | | 1.50 |
| (6) color solutions | q.s. | | 1.75 |
| | | | 1,137.1 |

While the foregoing examples are directed to compositions for the relief of premenstrual and menstrual discomforts, the novel combination of flavorings can be used with any of the active ingredients alone or in combination. Also, the sweetening and boding agent, high fructose corn syrup, may be replaced by sucrose or invert sugar syrup, with or without the addition of 70% sorbitol solutions.

We claim:

1. A liquid composition for the relief of premenstrual and menstrual discomfort comprising, as active pharmaceutical agents, an effective amount of an analgesic, an antihistamine, and a diuretic, said active agents being unpleasant in taste, and dissolved in a liquid vehicle, said composition containing 5-25 percent by volume alcohol and being flavored with active flavoring elements of citrus, vanilla, and mint, said active flavoring ingredients being present in an amount sufficient to mask the unpleasant taste of the pharmaceutically active agents.

2. A liquid composition as recited in claim 1 wherein the specific active pharmaceutical agents are acetaminophen, pyrilamine maleate, and pamabrom.

3. A liquid composition as recited in claim 1 wherein the said citrus flavoring ingredient is present from 0.09 to 0.31 percent by weight of the liquid composition, the vanilla flavoring ingredient is present in from 0.05 to 1.5 percent by weight of the liquid composition, and the said mint flavoring ingredient is present in an amount sufficient to mask the taste of the pharmaceutically active agents but in amount below the taste threshold of the intended subject.

4. A liquid composition as recited in claim 3 wherein the mint flavoring ingredient is present in from 0.02 to 0.16 percent by weight of the liquid composition.

5. A liquid composition as recited in claim 1 wherein the composition contains at least 30 percent corn syrup.

6. A liquid composition as recited in claim 1 wherein the composition contains at least 30% sucrose and sorbitol syrup.

7. A liquid composition as recited in claim 1 wherein the composition contains 15-25 percent alcohol.

8. A liquid composition for the relief of premenstrual and menstrual discomfort comprising, as active pharmaceutical agents, an effective amount of acetaminophen, pyrilamine maleate, and pamabrom, said active agents being dissolved in a liquid vehicle containing 12-25 percent by volume of alcohol and at least 30 percent by volume of corn syrup, and being flavored with from 0.09 to 0.31 percent of citrus flavoring ingredients, 0.05 to 1 5 percent of vanilla flavoring ingredients, and an amount of mint flavoring ingredients greater than that necessary to mask the unpleasant taste of the active pharmaceutical agents but less than the representing the taste threshold for mint of the ultimate subject.

9. A liquid composition as recited in claim 8 wherein the mint flavoring ingredient is present in from 0.02 to 0.16 percent by weight.

10. A liquid composition as recited in claim 8 wherein the citrus flavoring ingredient comprises 0.04 to 0.15 percent by weight of orange ingredients and from 0.05 to 0.16 percent by weight of lemon ingredients.

11. A liquid composition as recited in claim 8 wherein the citrus flavoring ingredient comprises from 0.06 to 0.09 percent by weight of orange ingredient and from 0.03 to 0.22 percent by weight of lemon ingredient.

12. A method for the relief of premenstrual and menstrual discomfort comprising administration, in the night, of an effective amount of a liquid composition comprising, as active pharmaceutical agents, an effective amount of acetaminophen, pyrilamine maleate, and pamabrom, said active agents being dissolved in a liquid vehicle, comprising 5 to 25 percent by volume of alcohol and at least 30 percent by weight corn syrup, and being flavored with from 0.09 to 0.31 percent of citrus flavoring ingredients, 0.05 to 1.5 percent of vanilla flavoring ingredients, and an amount of mint flavoring ingredients greater than that necessary to mask the unpleasant taste of the active pharmaceutical agents but less than the representing the taste threshold for mint of the ultimate subject.

* * * * *